(12) United States Patent
Anderson et al.

(10) Patent No.: US 11,975,199 B2
(45) Date of Patent: May 7, 2024

(54) PHASE-DEPENDENT BRAIN NEUROMODULATION OF CROSS-FREQUENCY COUPLING

(71) Applicant: The Johns Hopkins University, Baltimore, MD (US)

(72) Inventors: William S. Anderson, Towson, MD (US); Yousef Salimpour, Baltimore, MD (US); L. Leon Chen, New York, NY (US); Kelly Mills, Silver Spring, MD (US)

(73) Assignee: The Johns Hopkins University, Baltimore, MD (US)

( * ) Notice: Subject to any disclaimer, the term of this patent is extended or adjusted under 35 U.S.C. 154(b) by 294 days.

(21) Appl. No.: 17/310,445

(22) PCT Filed: Jan. 31, 2020

(86) PCT No.: PCT/US2020/016189
§ 371 (c)(1),
(2) Date: Aug. 3, 2021

(87) PCT Pub. No.: WO2020/163177
PCT Pub. Date: Aug. 13, 2020

(65) Prior Publication Data
US 2022/0118259 A1 Apr. 21, 2022

Related U.S. Application Data

(60) Provisional application No. 62/806,519, filed on Feb. 15, 2019, provisional application No. 62/800,841, filed on Feb. 4, 2019.

(51) Int. Cl.
*A61N 1/02* (2006.01)
*A61N 1/05* (2006.01)
*A61N 1/36* (2006.01)

(52) U.S. Cl.
CPC ......... *A61N 1/36139* (2013.01); *A61N 1/025* (2013.01); *A61N 1/0529* (2013.01);
(Continued)

(58) Field of Classification Search
CPC .. A61N 1/36139; A61N 1/025; A61N 1/0529; A61N 1/36171; A61N 1/36192;
(Continued)

(56) References Cited

U.S. PATENT DOCUMENTS

2007/0142874 A1* 6/2007 John ................. A61N 2/02
607/45
2008/0021342 A1* 1/2008 Echauz ............... A61B 5/37
600/544

FOREIGN PATENT DOCUMENTS

EP 2209523 B1 1/2018
KR 1020140042711 A 4/2014
KR 1020150062584 A 6/2015

OTHER PUBLICATIONS

International Search Report and Written Opinion—PCT/US2020/016189—ISA—dated May 21, 2020.

* cited by examiner

*Primary Examiner* — Carl H Layno
*Assistant Examiner* — Anh-Khoa N Dinh
(74) *Attorney, Agent, or Firm* — Harrity & Harrity, LLP

(57) ABSTRACT

A device may receive, from one or more electrodes, information identifying brain activity for a first time period. The device may predict, based on the information identifying the brain activity for the first time period, predicted brain activity for a second time period that is to occur after the first time period. The device may determine, based on the predicted brain activity for the second time period, a brain stimulus for the second time period, wherein the brain stimulus is associated with a frequency and a phase deter- (Continued)

mined based on the predicted brain activity for the second time period. The device may cause the brain stimulus to be applied in accordance with the frequency and the phase during the second time period.

20 Claims, 24 Drawing Sheets

(52) U.S. Cl.
CPC ..... *A61N 1/36171* (2013.01); *A61N 1/36192* (2013.01); *A61N 1/36196* (2013.01)

(58) Field of Classification Search
CPC ............ A61N 1/36196; A61N 1/36067; A61N 1/36082; A61N 1/0534; A61N 1/36025; A61N 1/36064; A61N 1/0456; A61N 1/0531; A61N 1/0551; A61N 1/3603; A61N 1/36062; A61N 1/36071; A61N 1/36135; A61N 1/36185; A61N 2/004; A61N 1/36031; A61N 1/36078; A61N 1/36096; A61N 1/0476; A61N 1/3606; A61N 1/36167; A61N 2/006; A61N 2/02; A61N 2005/0626; A61N 2005/0647; A61N 2005/0651; A61N 2005/0659; A61N 5/0618; A61N 5/0622; A61B 5/375; A61B 5/4836; A61B 5/369; A61B 5/291; A61B 5/374; A61B 5/245; A61B 5/316; A61B 5/165; A61B 5/377
See application file for complete search history.

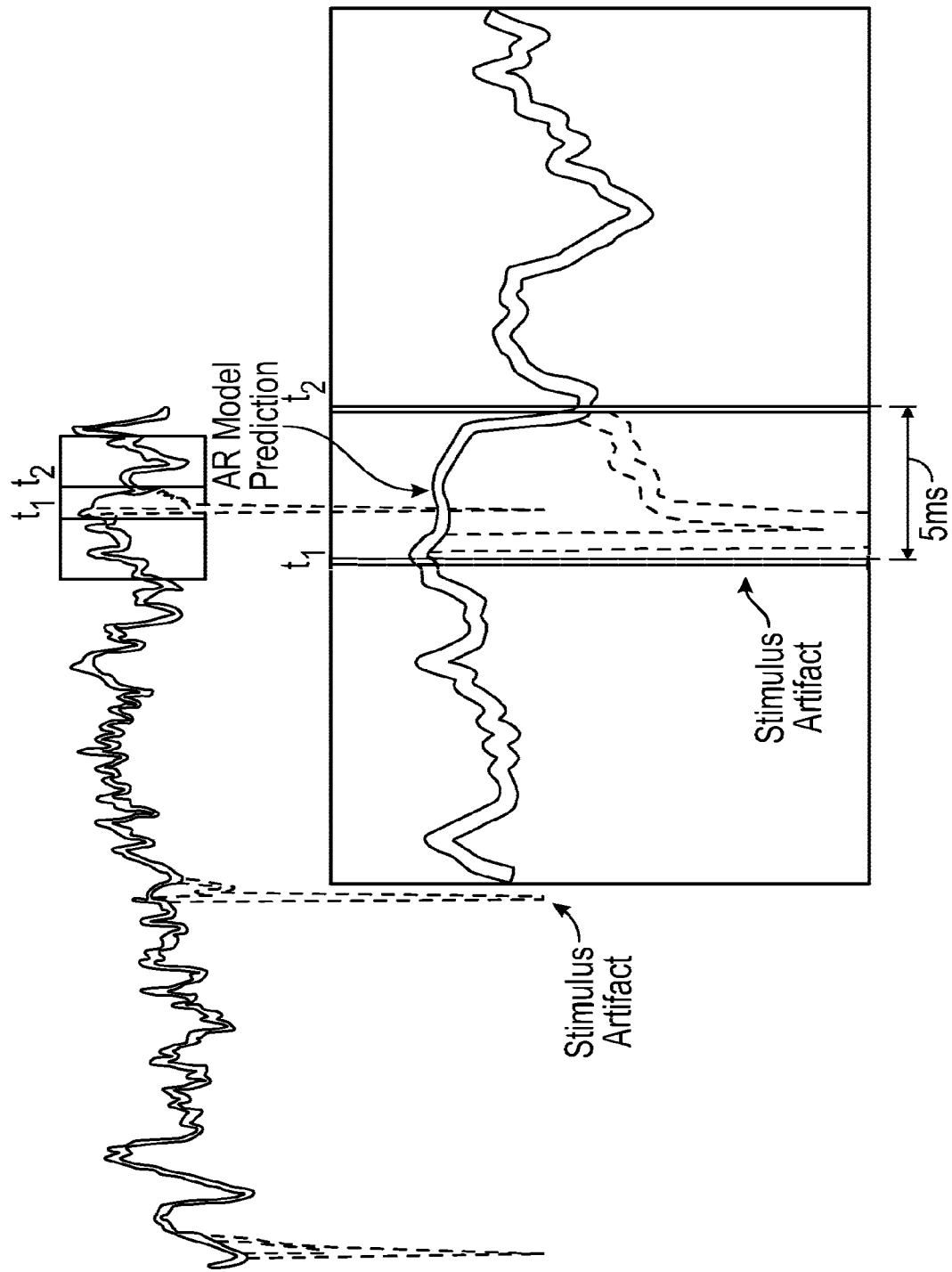

| Patient | Age, Year/Sex | Handedness/More Symptomatic side | Disease Duration, Year | Medications, Daily Total, mg (LED) | Hoehn & Yahr Stage | UPDRS Motor Score Off Medication | UPDRS Motor Score On Medication (% Improvement) |
|---|---|---|---|---|---|---|---|
| 1 | 63/M | R/R | 5 | 1000 | 2 | 36 | 10 (72) |
| 2 | 70/M | R/L | 12 | 3075 | 2.5 | 59 | 38 (36) |
| 3 | 56/M | R/R | 11 | 835 | 3 | 61 | 44 (30) |
| 4 | 72/M | R/R | 13 | 1200 | 2 | 47 | 37 (21) |
| 5 | 74/F | R/R | 4 | 900 | 3 | 74 | 58 (22) |

PHASE-DEPENDENT BRAIN NEUROMODULATION OF CROSS-FREQUENCY COUPLING

RELATED APPLICATIONS

This application is a 371 national stage of PCT Application No. PCT/US2020/016189 filed on Jan. 31, 2020, entitled "PHASE-DEPENDENT BRAIN NEUROMODULATION OF CROSS-FREQUENCY COUPLING," which claims priority to U.S. Provisional Patent Application No. 62/800,841, filed on Feb. 4, 2019, and entitled "PHASE-DEPENDENT BRAIN NEUROMODULATION OF CROSS-FREQUENCY COUPLING", and to U.S. Provisional Patent Application No. 62/806,519, filed on Feb. 15, 2019, and entitled "PHASE-DEPENDENT BRAIN NEUROMODULATION OF CROSS-FREQUENCY COUPLING," which are incorporated by reference herein in their entireties.

BACKGROUND

Brain stimulation may be used to alter, enhance, and/or improve brain function in neurological disorders, such as memory disorders, movement disorders, and/or the like. A control device may stimulate a brain of a patient by causing electrical stimulation pulses to be applied to the brain using a set of electrodes. The control device may trigger the electrodes to provide a constant, repeating set of electrical stimulation pulses, which may cause brain function to be altered, enhanced, and/or improved. The set of electrodes may be disposed on the patient's head, and may be connected to the control device via a set of wires.

SUMMARY

According to some implementations, a device may include one or more memories and one or more processors communicatively coupled to the one or more memories. The one or more processors may receive, from one or more electrodes, information identifying brain activity for a first time period. The one or more processors may predict, based on the information identifying the brain activity for the first time period, predicted brain activity for a second time period that is to occur after the first time period. The one or more processors may determine, based on the predicted brain activity for the second time period, a brain stimulus for the second time period, wherein the brain stimulus is associated with a frequency and a phase determined based on the predicted brain activity for the second time period. The one or more processors may cause the brain stimulus to be applied in accordance with the frequency and the phase during the second time period.

BRIEF DESCRIPTION OF THE DRAWINGS

FIGS. 5, 6, 7A-7E, 8, 9, 10A-10B, 11, 12, 13A-13C, 14A-14C, and 15 are diagrams relating to example implementations described herein.

DETAILED DESCRIPTION

The following detailed description of example implementations refers to the accompanying drawings. The same reference numbers in different drawings may identify the same or similar elements.

Electrical pulse-based brain stimulation may be performed using a fixed set of electrical pulses applied to a brain of a patient for a period of time. This technique may result in alteration, improvement, enhancement, and/or the like to brain function of the brain of the patient. However, using a constant set of electrical pulses may be inefficient, resulting in wasted energy resources, which may hinder miniaturization of brain stimulation devices. Moreover, using a fixed set of electrical pulses may result in relatively poor clinical outcomes. For example, using constant stimulation may result in lower thresholds for stimulation-associated side effects (e.g., as a result of activating or inhibiting structures proximate to locations at which the constant stimulation is applied).

Some implementations described herein use phase-dependent neuromodulation to reduce a utilization of energy resource, to improve a likelihood of positive patient outcomes from electrical pulse-based brain stimulation by modulating the cross-frequency coupling in the cortical structure, and/or the like. For example, a device may measure brain activity, predict future brain activity, dynamically identify a stimulus pulse to control the predicted future brain activity, and cause the stimulus pulse to be applied to correct an issue with the predicted future brain activity. Moreover, based on reducing a utilization of energy resources, some implementations described herein enable miniaturization and/or implantability of a device to perform phase-dependent neuromodulation. This technique may be applicable in treatment relating to Parkinson's disease, theta rhythm issues relating to memory, Schizophrenia, Alzheimer's disease, and/or the like.

Figure 1:
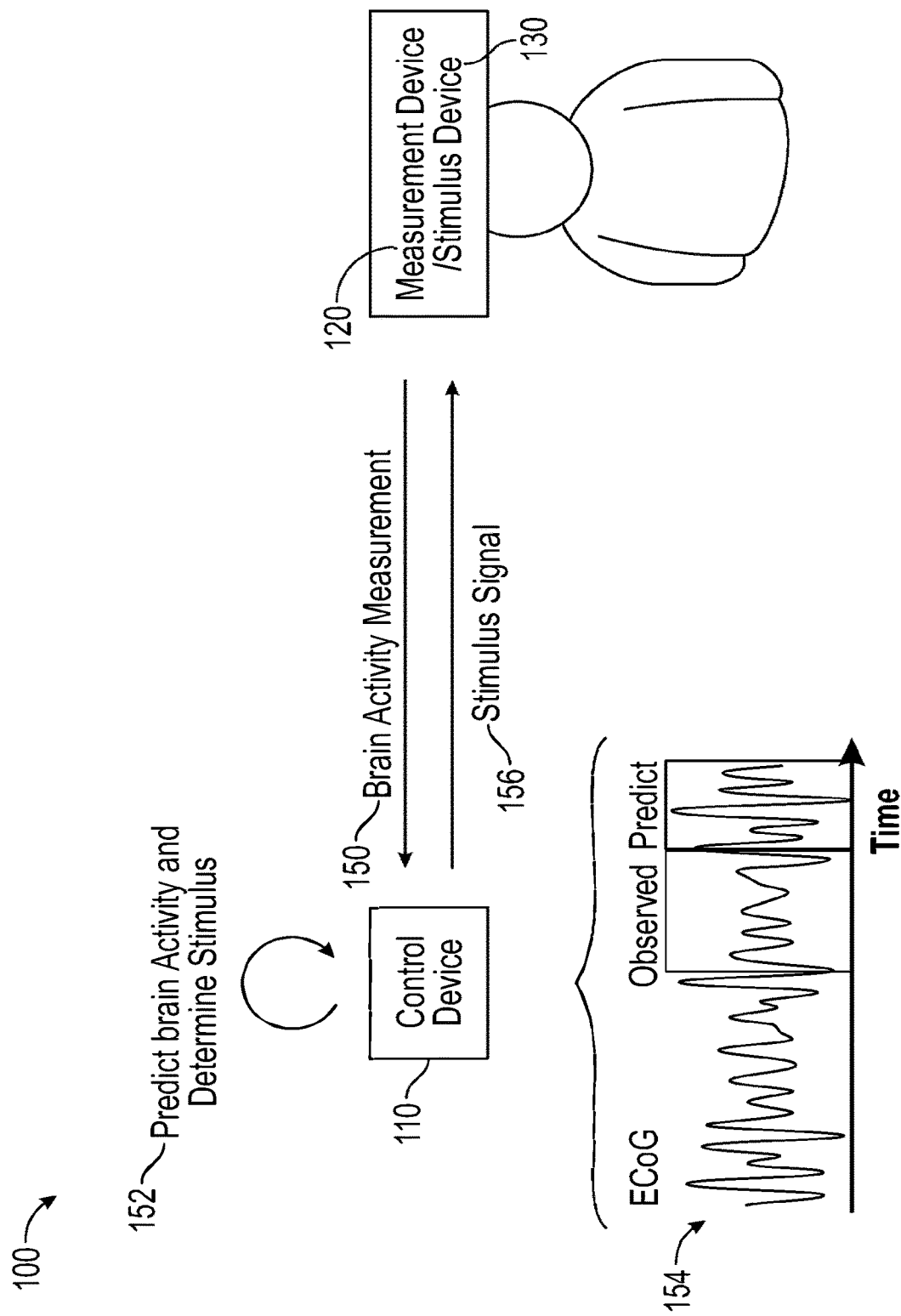
FIG. 1 is a diagram of an example implementation described herein.

FIG. 1 is a diagram of an example implementation 100 described herein. As shown in FIG. 1, example implementation 100 may include a control device 110 that communicates with a measurement device 120 and/or a stimulus device 130. In some implementations, control device 110 or another device may wirelessly power measurement device 120 and/or stimulus device 130 via a wireless power transmission functionality.

As further shown in FIG. 1, and by reference number 150, control device 110 may receive information identifying a brain activity measurement from measurement device 120. For example, control device 110 may receive information identifying a phase, amplitude, frequency, and/or the like of brain activity of a brain of a patient. In some implementations, control device 110 may receive information identifying brain activity for a particular time interval. In some implementations, control device 110 may determine whether a threshold level of brain activity is detected for the particular time interval. For example, control device 110 may determine that a threshold level of beta activity (e.g., activity in a range of 13 Hertz (Hz) to 30 Hz) is detected. In some implementations, control device 110 may provide a phase-dependent stimulation or a non-phase dependent stimulation (e.g., based on a forward prediction of brain activity) based on identifying a threshold level of beta activity. Additionally, or alternatively, control device 110 may determine that a threshold level of phase-amplitude coupling is detected. In this case, control device 110 may use a rolling dynamic phase amplitude coupling (PAC) estimation technique to determine the phase amplitude coupling in intervals of less than or equal to 1 second, 500 milliseconds, and/or the like. In this way, control device 110 may avoid performing complex calculations to predict brain activity when the brain activity is below a threshold for which corrective stimuli are to be applied, thereby reducing processor utilization, improving battery life, improving a lifespan of example implementation 100, and/or the like.

As further shown in FIG. 1, and by reference number 152, control device 110 may predict brain activity and determine a stimulus to apply to the brain of the patient. For example, and as shown by reference number 154, based on information identifying brain activity for a first time period, control device 110 may predict brain activity for a second time period occurring after the first time period. In this case, control device 110 may determine a set of electrical pulses to correspond to a predicted period of rhythmic brain activity. For example, control device 110 may determine the set of electric pulses based on signal predictive modeling of rhythmic activity with forward-prediction to time the set of electric pulses in accordance with the rhythmic activity. Some examples may include using auto-regressive modeling, generalized linear modeling, machine learning-based modeling, and/or the like. In this way, control device 110 enables electrical pulse-based brain stimulation using reduced power and with improved efficacy relative to a constant set of brain rhythmic activities.

In some implementations, control device 110 may remove one or more artifacts from measured brain activity when determining predicted brain activity. For example, control device 110 may identify one or more artifacts in brain activity during a first time period corresponding to one or more electrical pulses provided during the first time period, and may remove the one or more artifacts in the brain activity to determine baseline brain activity without the one or more electrical pulses. In some implementations, control device 110 may predict the artifacts using signal predictive modeling to interpolate brain activity during periods when artifacts occur as a result of application of phase-dependent stimulus pulses. In this case, control device 110 may predict subsequent brain activity based on the baseline brain activity, thereby improving accuracy of a subsequent brain activity prediction relative to predicting with the artifacts included. In some implementations, control device 110 may use a parametric spectral estimation technique to predict brain activity. For example, control device 110 may model band limited oscillations in brain activity using the parametric spectral estimation technique, and may predict subsequent brain activity based on modeling band limited oscillations in brain activity. In some implementations, control device 110 may apply a band-pass optimized autoregressive technique to predict brain activity.

As further shown in FIG. 1, and by reference number 156, control device 110 may provide a stimulus signal to stimulus device 130. For example, control device 110 may cause stimulus device 130 to provide a set of electrical pulses to the brain of the patient during the predicted period of rhythmic brain activity. In this way, control device 110 enables phase-dependent neuromodulation. In some implementations, the set of electrical pulses may be timed in accordance with a phase of brain activity (e.g., within a particular band of oscillatory frequencies), a frequency of brain activity, and/or the like predicted based on past brain activity. In some implementations, control device 110 may cause stimulus device 130 to provide a variable-pulse stimulus. For example, control device 110 may cause electrical pulses to vary in frequency, phase, intensity, and/or the like, thereby enabling reduced power utilization, improved efficacy, and/or the like relative to a constant set of electrical pulses.

As indicated above, FIG. 1 is provided merely as one or more examples. Other examples may differ from what is described with regard to FIG. 1.

Figure 2:
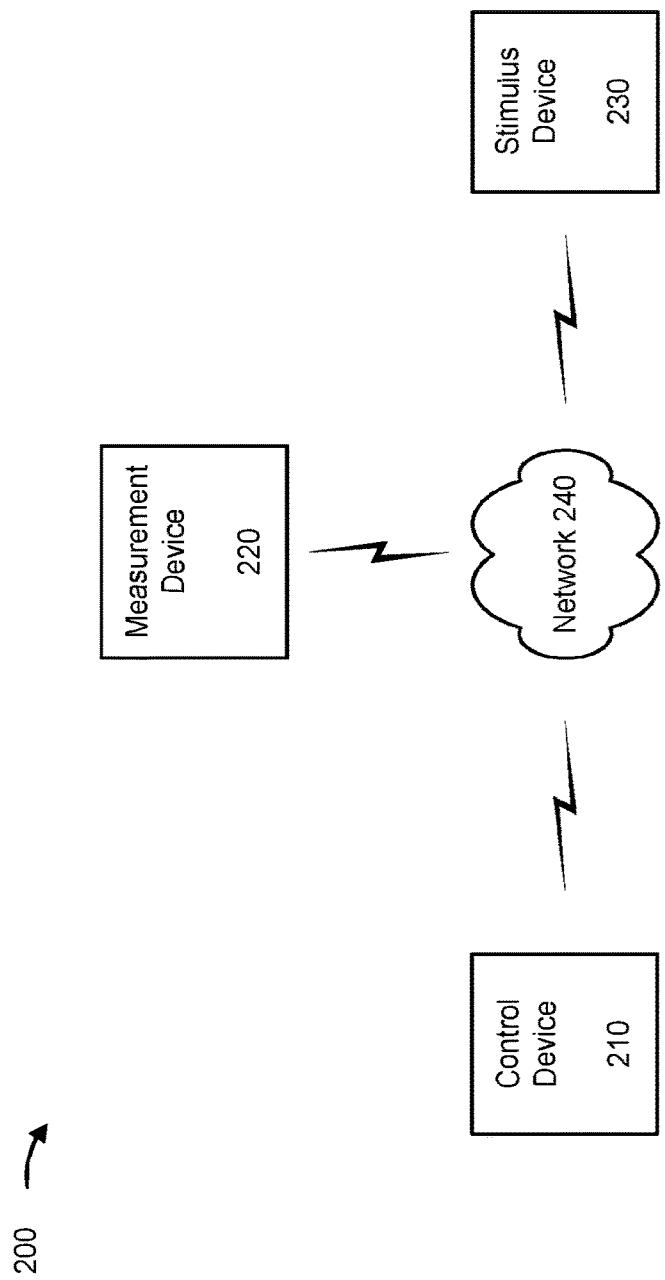
FIG. 2 is a diagram of an example environment in which systems and/or methods described herein may be implemented.

FIG. 2 is a diagram of an example environment 200 in which systems and/or methods described herein may be implemented. As shown in FIG. 2, environment 200 may include a control device 210, a measurement device 220, a stimulus device 230, and a network 240. Devices of environment 200 may interconnect via wired connections, wireless connections, or a combination of wired and wireless connections (e.g., for power transmission, data transmission, and/or the like).

Control device 210 includes one or more devices capable of receiving, generating, storing, processing, and/or providing information associated with phase-dependent neuromodulation. For example, control device 210 may include a communication and/or computing device, such as a computer (e.g., a desktop computer, a laptop computer, a tablet computer, a handheld computer), a medical device, a wearable communication device (e.g., a smart wristwatch, a pair of smart eyeglasses, a wearable medical device, an implantable medical device, etc.), or a similar type of device. In some implementations, control device 210 may be an external device connected to measurement device 220 and/or stimulus device 230. In some implementations, control device 210, measurement device 220, and stimulus device 230 may be an integrated system-on-chip device that is at least partially implanted into a patient.

Measurement device 220 includes one or more devices capable of receiving, generating, storing, processing, and/or providing information associated with a measurement of brain activity. For example, measurement device 220 may include an electrode (e.g., a measurement electrode) for sensing a phase, a frequency, an amplitude, cross-frequency coupling, and/or the like of brain activity of a brain of a patient. In some implementations, measurement device 220 may be a measurement device mounted onto a head of a patient, a measurement device surgically implanted into a head of a patient, and/or the like.

Stimulus device 230 includes one or more devices capable of receiving, generating, storing, processing, and/or providing information associated with stimulation of a brain. For example, stimulus device 230 may include an electrode (e.g., a stimulus electrode) or multiple electrodes for applying an electrical pulse to a brain of a patient. In some implementations, stimulus device 230 may be a stimulation device mounted onto a head of a patient, a stimulation device surgically implanted into a head of a patient, and/or the like.

Network 240 includes one or more wired and/or wireless networks. For example, network 240 may include a cellular network (e.g., a long-term evolution (LTE) network, a code division multiple access (CDMA) network, a 3G network, a 4G network, a 5G network, another type of next generation network, etc.), a public land mobile network (PLMN), a local area network (LAN), a wide area network (WAN), a metropolitan area network (MAN), a telephone network (e.g., the Public Switched Telephone Network (PSTN)), a private network, an ad hoc network, an intranet, the Internet, a fiber optic-based network, a cloud computing network, or the like, and/or a combination of these or other types of networks.

The number and arrangement of devices and networks shown in FIG. 2 are provided as one or more examples. In practice, there may be additional devices and/or networks, fewer devices and/or networks, different devices and/or networks, or differently arranged devices and/or networks than those shown in FIG. 2. Furthermore, two or more devices shown in FIG. 2 may be implemented within a single device, or a single device shown in FIG. 2 may be implemented as multiple, distributed devices. Additionally, or alternatively, a set of devices (e.g., one or more devices) of environment 200 may perform one or more functions described as being performed by another set of devices of environment 200.

Figure 3:
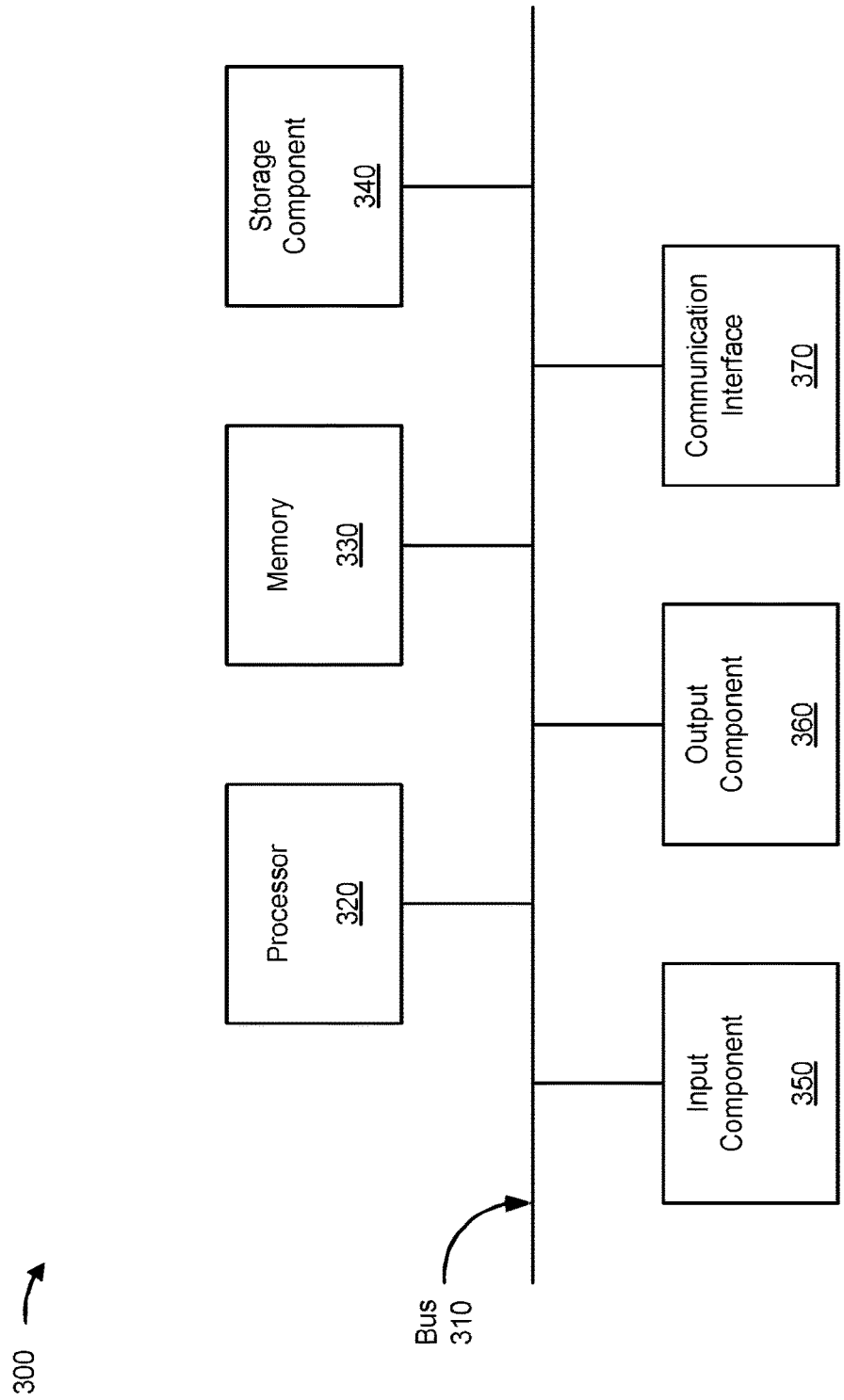
FIG. 3 is a diagram of example components of one or more devices of FIG. 2.

FIG. 3 is a diagram of example components of a device 300. Device 300 may correspond to control device 210, measurement device 220, and/or stimulus device 230. In some implementations, control device 210, measurement device 220, and/or stimulus device 230 may include one or more devices 300 and/or one or more components of device 300. As shown in FIG. 3, device 300 may include a bus 310, a processor 320, a memory 330, a storage component 340, an input component 350, an output component 360, and a communication interface 370.

Bus 310 includes a component that permits communication among multiple components of device 300. Processor 320 is implemented in hardware, firmware, and/or a combination of hardware and software. Processor 320 is a central processing unit (CPU), a graphics processing unit (GPU), an accelerated processing unit (APU), a microprocessor, a microcontroller, a digital signal processor (DSP), a field-programmable gate array (FPGA), an application-specific integrated circuit (ASIC), or another type of processing component. In some implementations, processor 320 includes one or more processors capable of being programmed to perform a function. Memory 330 includes a random access memory (RAM), a read only memory (ROM), and/or another type of dynamic or static storage device (e.g., a flash memory, a magnetic memory, and/or an optical memory) that stores information and/or instructions for use by processor 320.

Storage component 340 stores information and/or software related to the operation and use of device 300. For example, storage component 340 may include a hard disk (e.g., a magnetic disk, an optical disk, and/or a magneto-optic disk), a solid state drive (SSD), a compact disc (CD), a digital versatile disc (DVD), a floppy disk, a cartridge, a magnetic tape, and/or another type of non-transitory computer-readable medium, along with a corresponding drive.

Input component 350 includes a component that permits device 300 to receive information, such as via user input (e.g., a touch screen display, a keyboard, a keypad, a mouse, a button, a switch, and/or a microphone). Additionally, or alternatively, input component 350 may include a component for determining location (e.g., a global positioning system (GPS) component) and/or a sensor (e.g., an accelerometer, a gyroscope, an actuator, another type of positional or environmental sensor, and/or the like). Output component 360 includes a component that provides output information from device 300 (via, e.g., a display, a speaker, a haptic feedback component, an audio or visual indicator, and/or the like).

Communication interface 370 includes a transceiver-like component (e.g., a transceiver, a separate receiver, a separate transmitter, and/or the like) that enables device 300 to communicate with other devices, such as via a wired connection, a wireless connection, or a combination of wired and wireless connections. Communication interface 370 may permit device 300 to receive information from another device and/or provide information to another device. For example, communication interface 370 may include an Ethernet interface, an optical interface, a coaxial interface, an infrared interface, a radio frequency (RF) interface, a universal serial bus (USB) interface, a Wi-Fi interface, a cellular network interface, and/or the like.

Device 300 may perform one or more processes described herein. Device 300 may perform these processes based on processor 320 executing software instructions stored by a non-transitory computer-readable medium, such as memory 330 and/or storage component 340. As used herein, the term "computer-readable medium" refers to a non-transitory memory device. A memory device includes memory space within a single physical storage device or memory space spread across multiple physical storage devices.

Software instructions may be read into memory 330 and/or storage component 340 from another computer-readable medium or from another device via communication interface 370. When executed, software instructions stored in memory 330 and/or storage component 340 may cause processor 320 to perform one or more processes described herein. Additionally, or alternatively, hardware circuitry may be used in place of or in combination with software instructions to perform one or more processes described herein. Thus, implementations described herein are not limited to any specific combination of hardware circuitry and software.

The number and arrangement of components shown in FIG. 3 are provided as an example. In practice, device 300 may include additional components, fewer components, different components, or differently arranged components than those shown in FIG. 3. Additionally, or alternatively, a set of components (e.g., one or more components) of device 300 may perform one or more functions described as being performed by another set of components of device 300.

Figure 4:
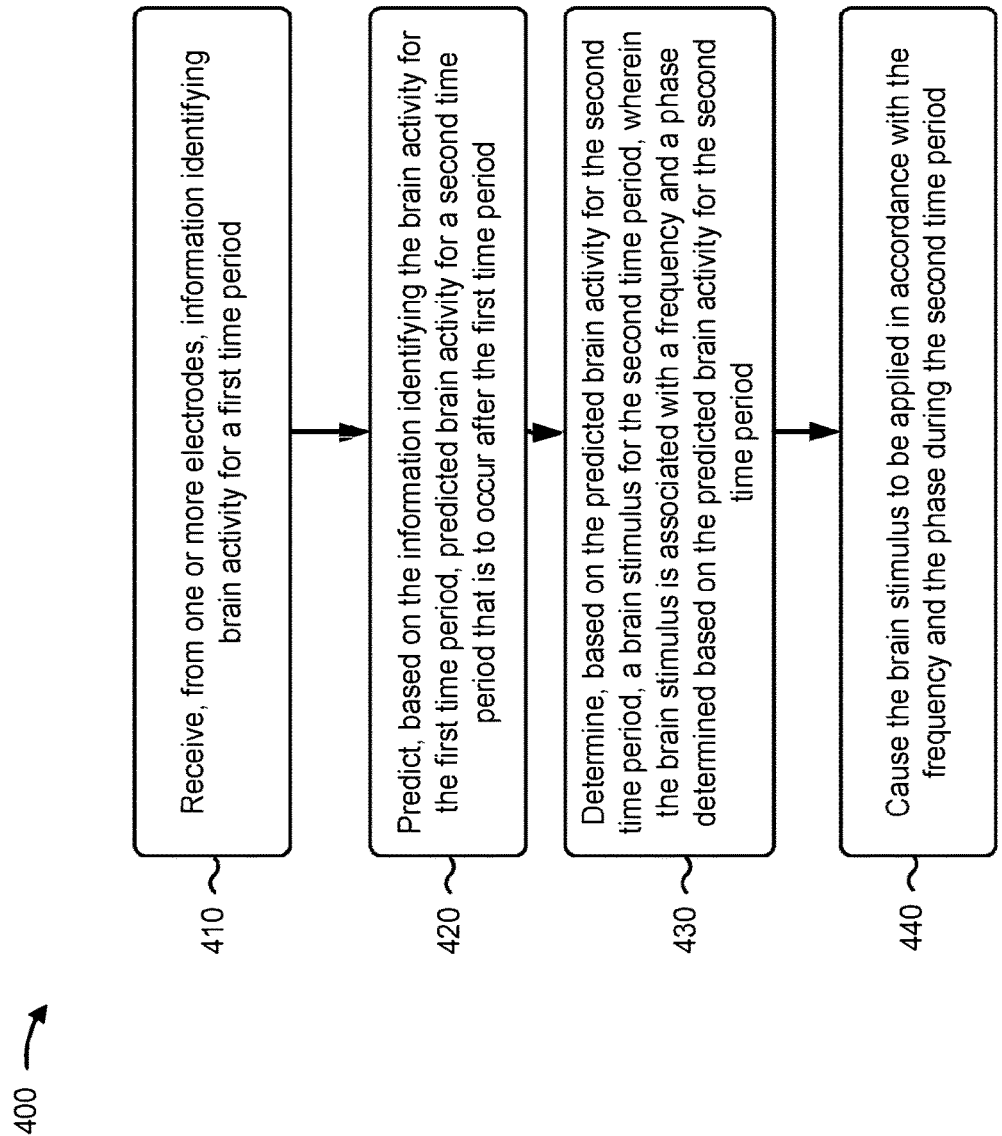
FIG. 4 is a flow chart of an example process for phase-dependent neuromodulation.

FIG. 4 is a flow chart of an example process 400 for phase-dependent neuromodulation. In some implementations, one or more process blocks of FIG. 4 may be performed by a control device (e.g., control device 210). In some implementations, one or more process blocks of FIG. 4 may be performed by another device or a group of devices separate from or including the control device, such as a measurement device (e.g., measurement device 220), a stimulus device (e.g., stimulus device 230), and/or the like.

As shown in FIG. 4, process 400 may include receiving, from one or more electrodes, information identifying brain activity for a first time period (block 410). For example, the control device (e.g., using processor 320, memory 330, storage component 340, input component 350, communication interface 370, and/or the like) may receive, from one or more electrodes, information identifying brain activity for a first time period, as described above.

As further shown in FIG. 4, process 400 may include predicting, based on the information identifying the brain activity for the first time period, predicted brain activity for a second time period that is to occur after the first time period (block 420). For example, the control device (e.g., using processor 320, memory 330, storage component 340, communication interface 370, and/or the like) may predict, based on the information identifying the brain activity for the first time period, predicted brain activity for a second time period that is to occur after the first time period, as described above.

As further shown in FIG. 4, process 400 may include determining, based on the predicted brain activity for the second time period, a brain stimulus for the second time period, wherein the brain stimulus is associated with a frequency and a phase determined based on the predicted brain activity for the second time period (block 430). For example, the control device (e.g., using processor 320, memory 330, storage component 340, communication interface 370, and/or the like) may determine, based on the predicted brain activity for the second time period, a brain stimulus for the second time period, as described above. In some implementations, the brain stimulus is associated with a frequency and a phase determined based on the predicted brain activity for the second time period.

As further shown in FIG. 4, process 400 may include causing the brain stimulus to be applied in accordance with the frequency and the phase during the second time period (block 440). For example, the control device (e.g., using processor 320, memory 330, storage component 340, output component 360, communication interface 370, and/or the like) may cause the brain stimulus to be applied in accordance with the frequency and the phase during the second time period, as described above.

Process 400 may include additional implementations, such as any single implementation or any combination of implementations described below and/or in connection with one or more other processes described elsewhere herein.

In a first implementation, the control device may determine an artifact during the first time period associated with a prior brain stimulus; determine an artifact-removed brain activity for the first time period based on the artifact; and predict the brain activity for the second time period based on the artifact-removed brain activity.

In a second implementation, alone or in combination with the first implementation, the phase is a selected phase of a detected brain rhythmic activity, and the brain stimulus includes one or more pulses timed in accordance with the phase.

In a third implementation, alone or in combination with one or more of the first and second implementations, the brain stimulus is caused to occur during a period of rhythmic brain activity in accordance with the frequency.

In a fourth implementation, alone or in combination with one or more of the first through third implementations, the brain stimulus is a variable-pulse stimulus.

In a fifth implementation, alone or in combination with one or more of the first through fourth implementations, the control device may predict the brain activity using a parametric spectral estimation technique for modeling band limited oscillations.

In a sixth implementation, alone or in combination with one or more of the first through fifth implementations, the control device may predict the brain activity using a bandpass optimized autoregressive technique.

In a seventh implementation, alone or in combination with one or more of the first through sixth implementations, the control device is an external device connected to one or more electrodes disposed onto a brain of a patient.

In an eighth implementation, alone or in combination with one or more of the first through seventh implementations, the control device is a system-on-chip device at least partially implanted into a patient.

In a ninth implementation, alone or in combination with one or more of the first through eighth implementations, process 400 may include determining that the brain activity for the first time period satisfies a threshold and predicting the brain activity for the second time period based at least in part on the brain activity for the first time period satisfying the threshold.

In a tenth implementation, alone or in combination with one or more of the first through ninth implementations, the threshold is a beta activity threshold.

In an eleventh implementation, alone or in combination with one or more of the first through tenth implementations the threshold is a phase amplitude coupling threshold.

In a twelfth implementation, alone or in combination with one or more of the first through eleventh implementations, determining the brain activity includes estimating a phase amplitude coupling in the first time period using a rolling dynamic phase amplitude coupling (PAC) estimation technique.

In a thirteenth implementation, alone or in combination with one or more of the first through twelfth implementations the phase amplitude coupling is estimated in a window of less than or equal to 1 second.

In a fourteenth implementation, alone or in combination with one or more of the first through thirteenth implementations, the phase amplitude coupling is estimated in a window of less than or equal to 500 milliseconds.

Although FIG. 4 shows example blocks of process 400, in some implementations, process 400 may include additional blocks, fewer blocks, different blocks, or differently arranged blocks than those depicted in FIG. 4. Additionally, or alternatively, two or more of the blocks of process 400 may be performed in parallel.

Figure 5:
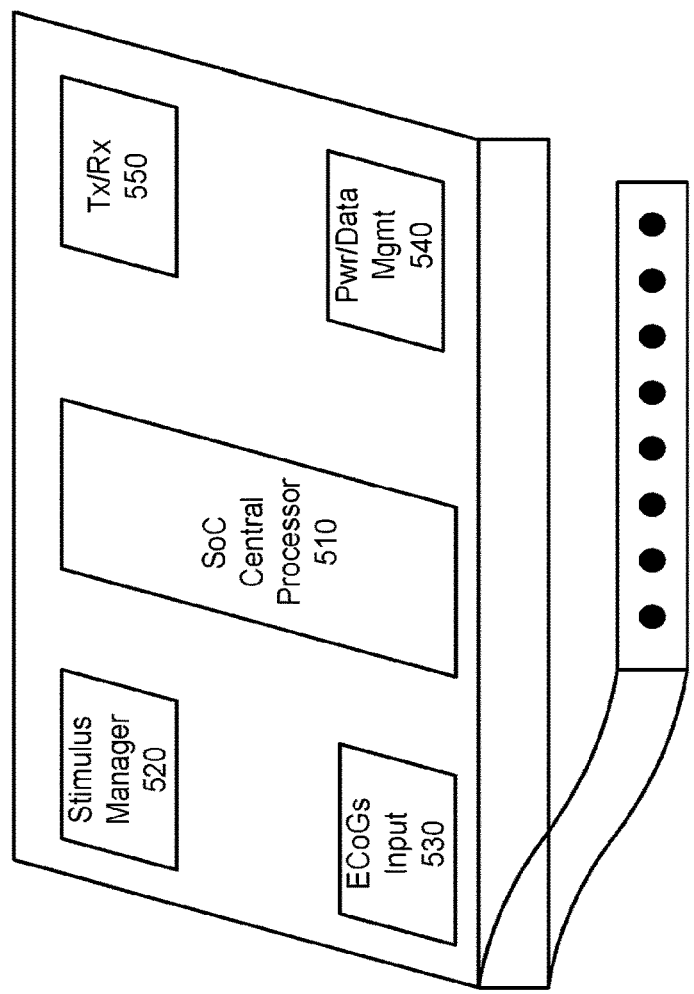

FIG. 5 is a diagram of an example implementation 500 of a neuromodulation system described herein.

As shown in FIG. 5, example implementation 500 may include a system-on-chip (SoC) central processor 510 that communicates with a stimulus manager 520, a set of electrocorticography (ECoGs) inputs 530, and a power and data manager 540 (e.g., which is connected to a power and data transmission and reception coil 550). In some implementations, SoC central processor 510 may include a memory, a data storage, a set of encoders and/or decoders, a direct memory access, a central processing unit (e.g., to provide peripheral interfacing, parameter estimation, and/or the like), a field programmable gate array (e.g., to perform artifact removal, spectral estimation, frequency band limitation, forward prediction, frequency and phase estimation, and/or the like), an analog mixed signal module, a communication unit (e.g., Ethernet, universal serial bus, etc.), a display, and/or the like. Example implementation 500 may provide an input channel interface and may enable multiple analog ECoG input recordings in connection with real-time stimulation at specific phases of a selected recording channel.

As indicated above, FIG. 5 is provided merely as one or more examples. Other examples may differ from what is described with regard to FIG. 5.

Figure 6:
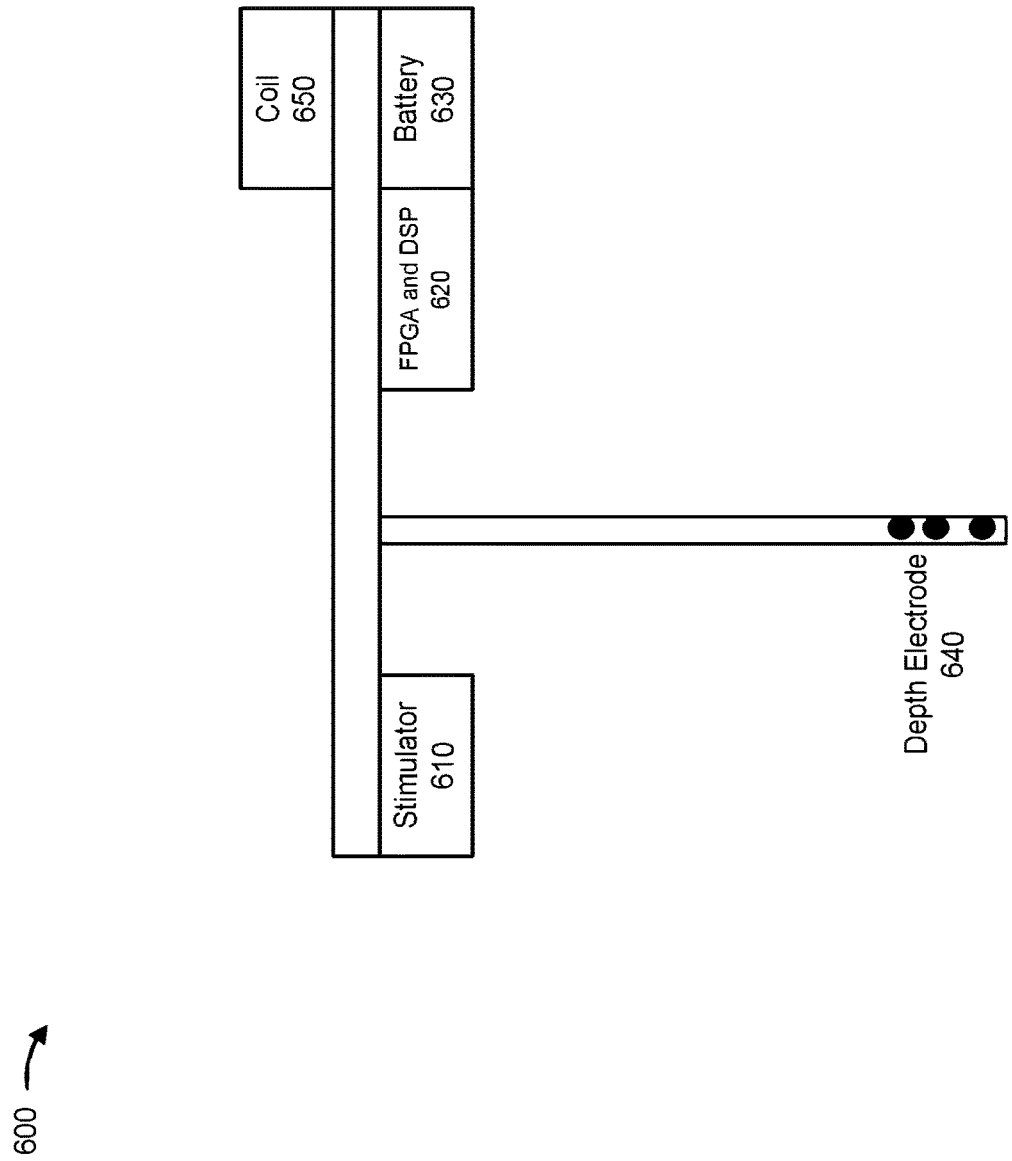

FIG. 6 is a diagram of an example implementation 600 of a cortical and subcortical stimulation system described herein.

As shown in FIG. 6, example implementation 600 may include a stimulator 610, a field programmable gate array (FPGA) and digital signal processor (DSP) 620, a battery 630, a depth electrode 640, and a coil 650. In some implementations, stimulator 610 may generate a stimulus that is applied using depth electrode 640 based on information from field programmable gate array and digital signal processor 620. For example, field programmable gate array and digital signal processor 620 may receive a measurement of brain activity from depth electrode 640, predict subsequent brain activity, and determine a stimulus that stimulator 610 is to cause depth electrode 640 to apply. Battery 630 may connect to coil 650, which may be a wireless bidirectional coil to enable wireless charging of example implementation 600. In some implementations, coil 650 may also enable wireless communication between example implementation 600 and an external control or monitoring device to enable patient monitoring, device updating, and/or the like.

As indicated above, FIG. 6 is provided merely as one or more examples. Other examples may differ from what is described with regard to FIG. 6.

FIGS. 7A-7E are diagrams relating to example implementations described herein.

Figure 7A:
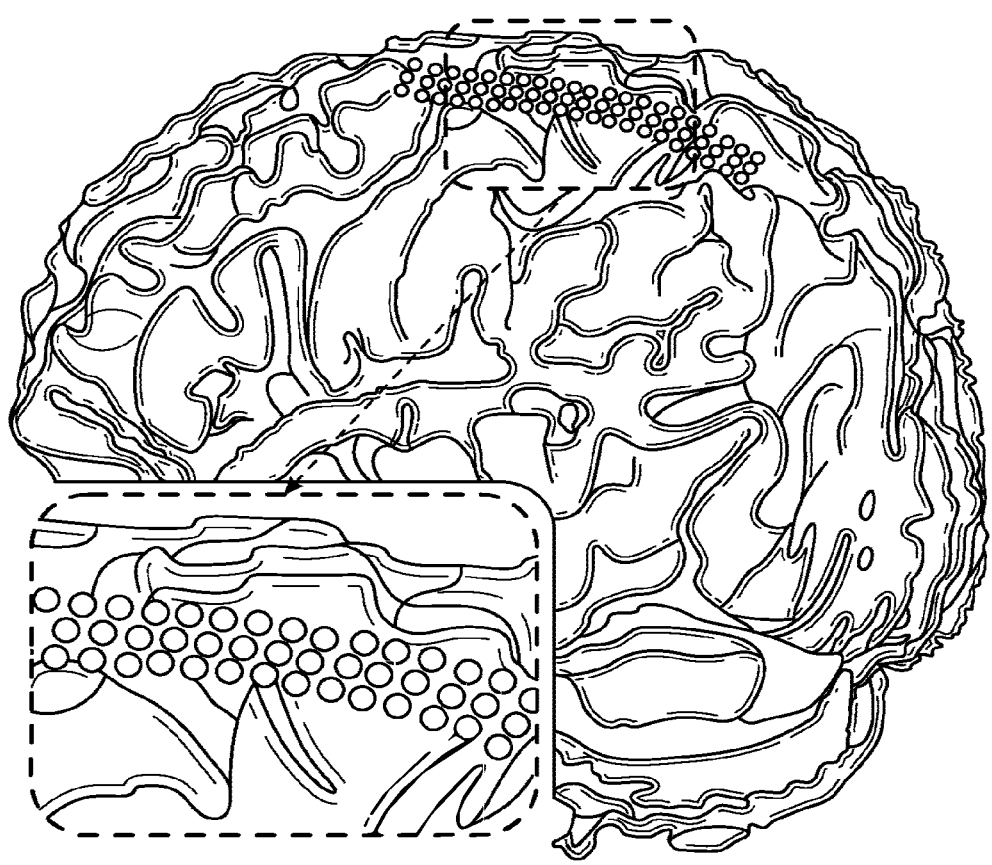
Figure 7B:
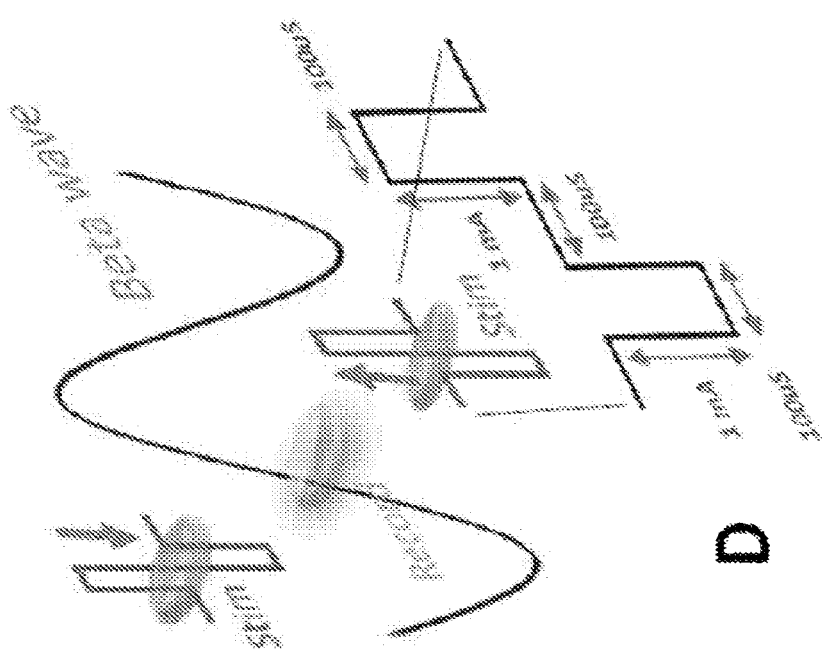
Figure 7C:
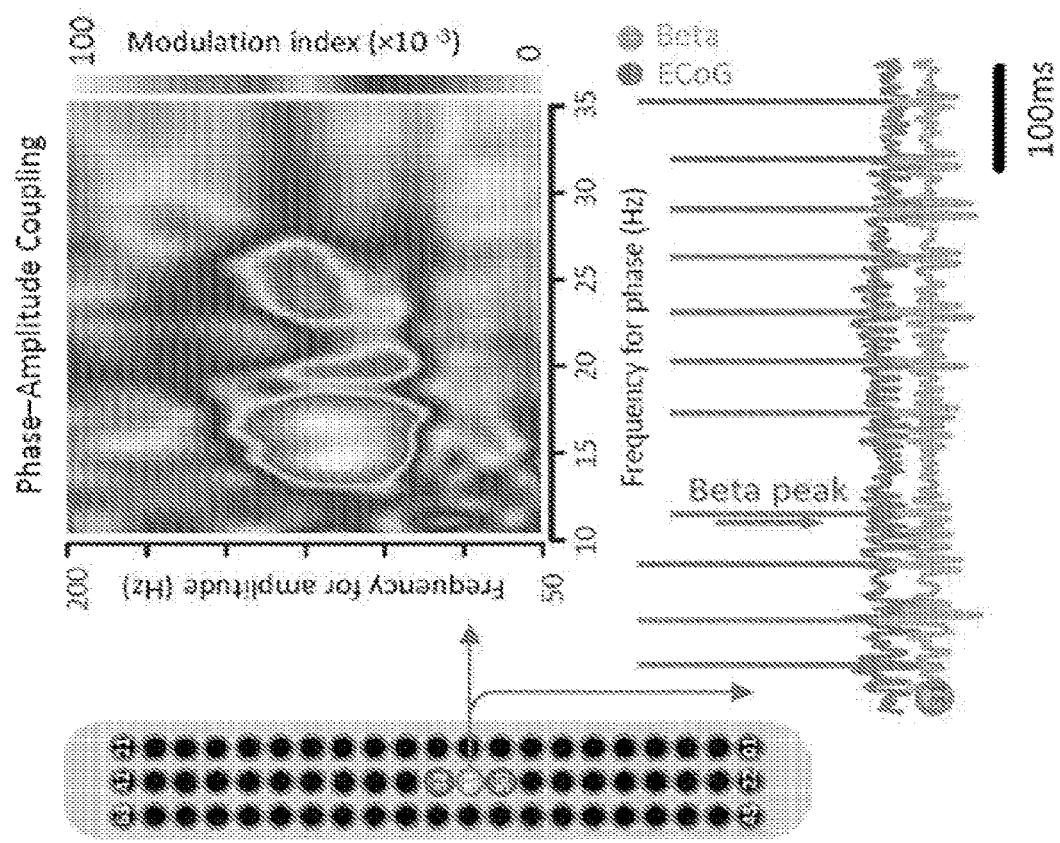
Figure 7D:
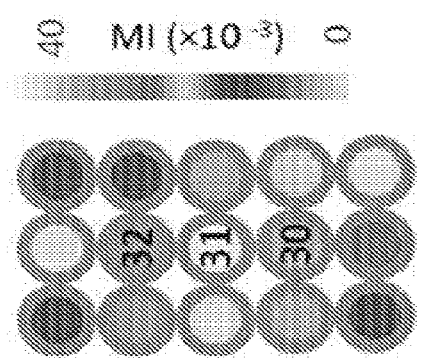
Figure 7E:
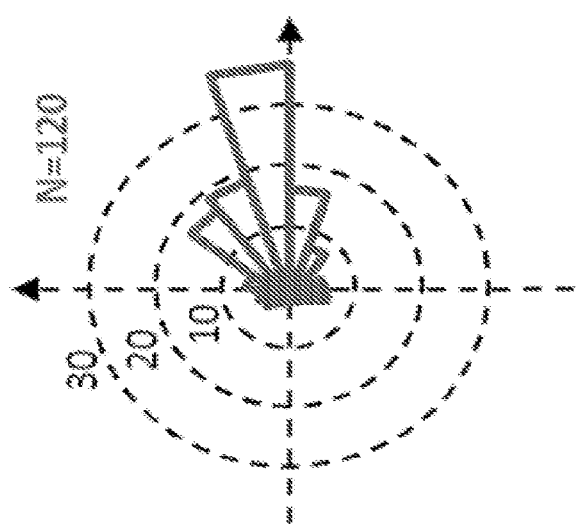

As shown in FIG. 7A, electrode coordinates of an implanted cortical strip are estimated using imaging data. The relative location of the strip electrode contacts with respect to the site of recording is shown for the sample subjects. FIG. 7B shows an example of motor cortex oscillation in the beta range (e.g., 10-35 Hertz (Hz)). Electrical stimulation pulse trains are delivered at configured phases of the oscillation (e.g., a peak phase) in a biphasic and bipolar configuration. FIG. 7C shows an overview of the stimulation application provided by a strip of electrodes including selected contacts for recording and bipolar stimulation. Further, FIG. 7C, shows an example of waveforms including the timing of the phase-dependent stimulation pulses produced by the strip of electrodes. FIG. 7D shows an example of an average modulation index (MI) across responsive contacts over a motor cortex area. A selected contact may be the one with a maximum average MI. E. By estimating the instantaneous phase and frequency of the beta band at the stimulation time points, the overall performance of the phase-dependent stimulation algorithm at the peak of the theta and beta rhythm are summarized in the plot of FIG. 7E.

As indicated above, FIGS. 7A-7E are provided merely as one or more examples. Other examples may differ from what is described with regard to FIGS. 7A-7E.

Figure 8:
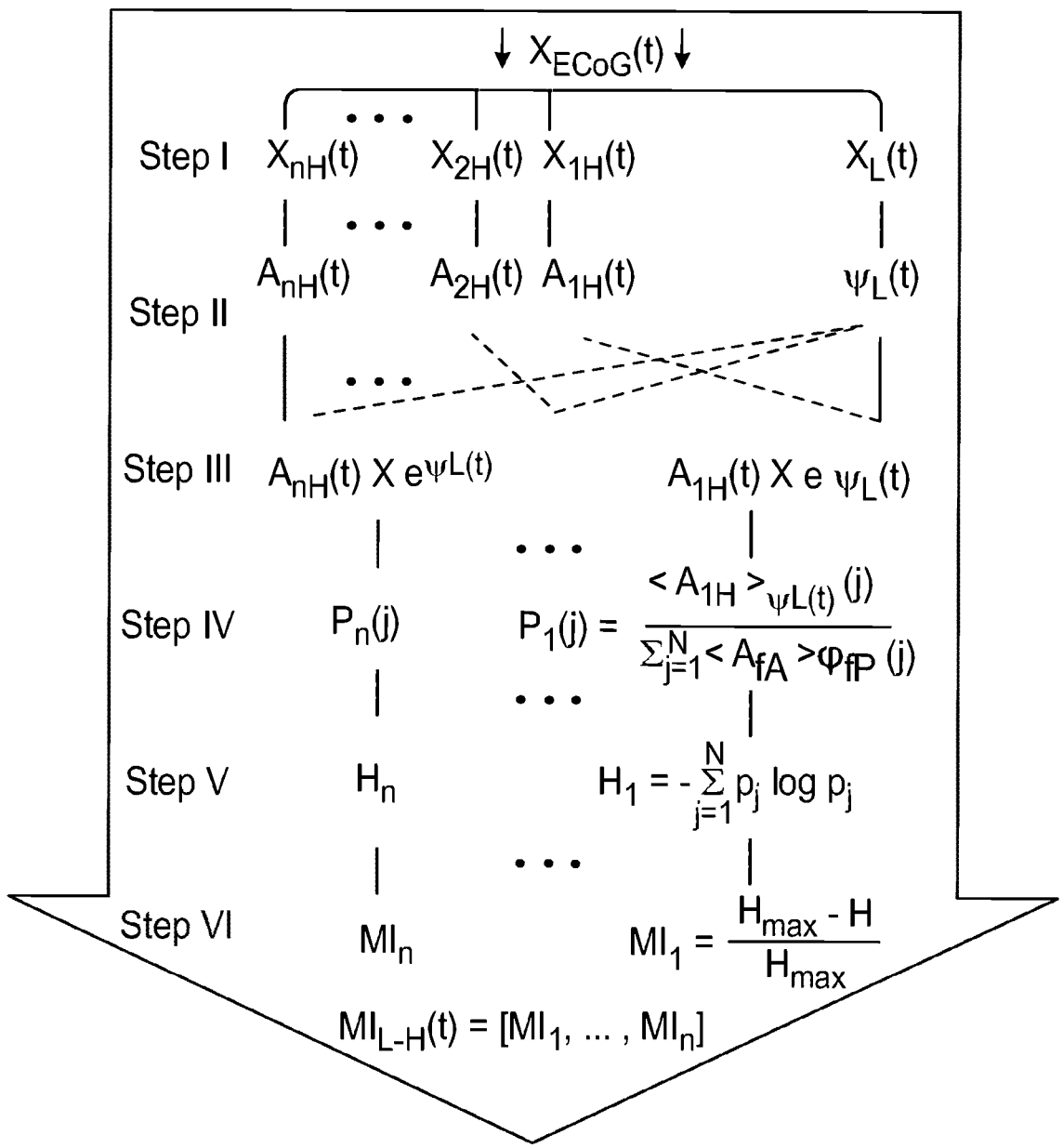

FIG. 8 is a diagram of a process 800 relating to example implementations described herein.

FIG. 8 shows an example of steps for dynamic phase-amplitude coupling (PAC) estimation. Process 800 for estimating the dynamic low frequency phase modulated high frequency power may include, for example, (Step I) decomposition of an electrocorticography (ECoG) segment into a low frequency component and a set of high frequency band components with a 10 Hz step size. In some implementations, process 800 may include (Step II) phase of low frequency component and amplitude envelope of the high frequency series are obtained from the standard Hilbert transform. In some implementations, process 800 may include (Step III) two dimensional signals are generated, which include the amplitude of each high frequency component with respect to the phase of the low frequency. In some implementations, process 800 may include (Step IV) the normalized mean amplitude of the high frequency components are computed at each bin of the low frequency phase. In some implementations, process 800 may include (Step V) an entropy measure is calculated based on these normalized values. In some implementations, process 800 may include (Step VI) the MI is estimated by normalizing the entropy measures to the maximum possible entropy value and, finally the low frequency phase modulated high frequency power vector is considered by labeling all the MI values as ordered components of the vector.

As indicated above, FIG. 8 is provided merely as an example. Other examples may differ from what is described with regard to FIG. 8.

Figure 9:
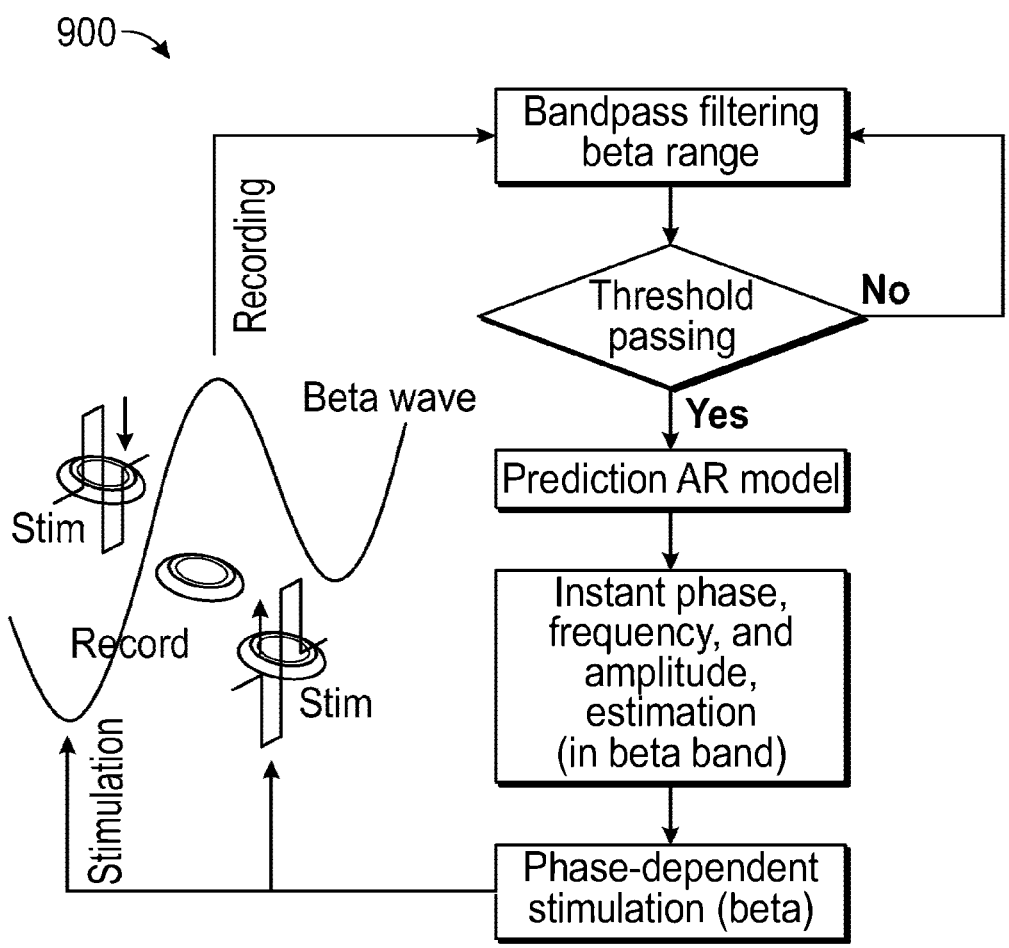

FIG. 9 is a diagram of a process 900 relating to example implementations described herein.

Process 900 enables phase-dependent motor cortex stimulation using cortically implanted grid electrodes. Process 900 may provide for phase-dependent stimulation for modulation of the beta phase and gamma amplitude coupling over the motor cortex. Process 900 includes, in some implementations, bandpass filter and beta range determination, threshold passing determination, prediction using an auto-regressive model (or another type of model), instantaneous phase, frequency, and amplitude estimation in a beta band, and phase-dependent stimulation in the beta band.

As indicated above, FIG. 9 is provided merely as an example. Other examples may differ from what is described with regard to FIG. 9.

Figure 10B:
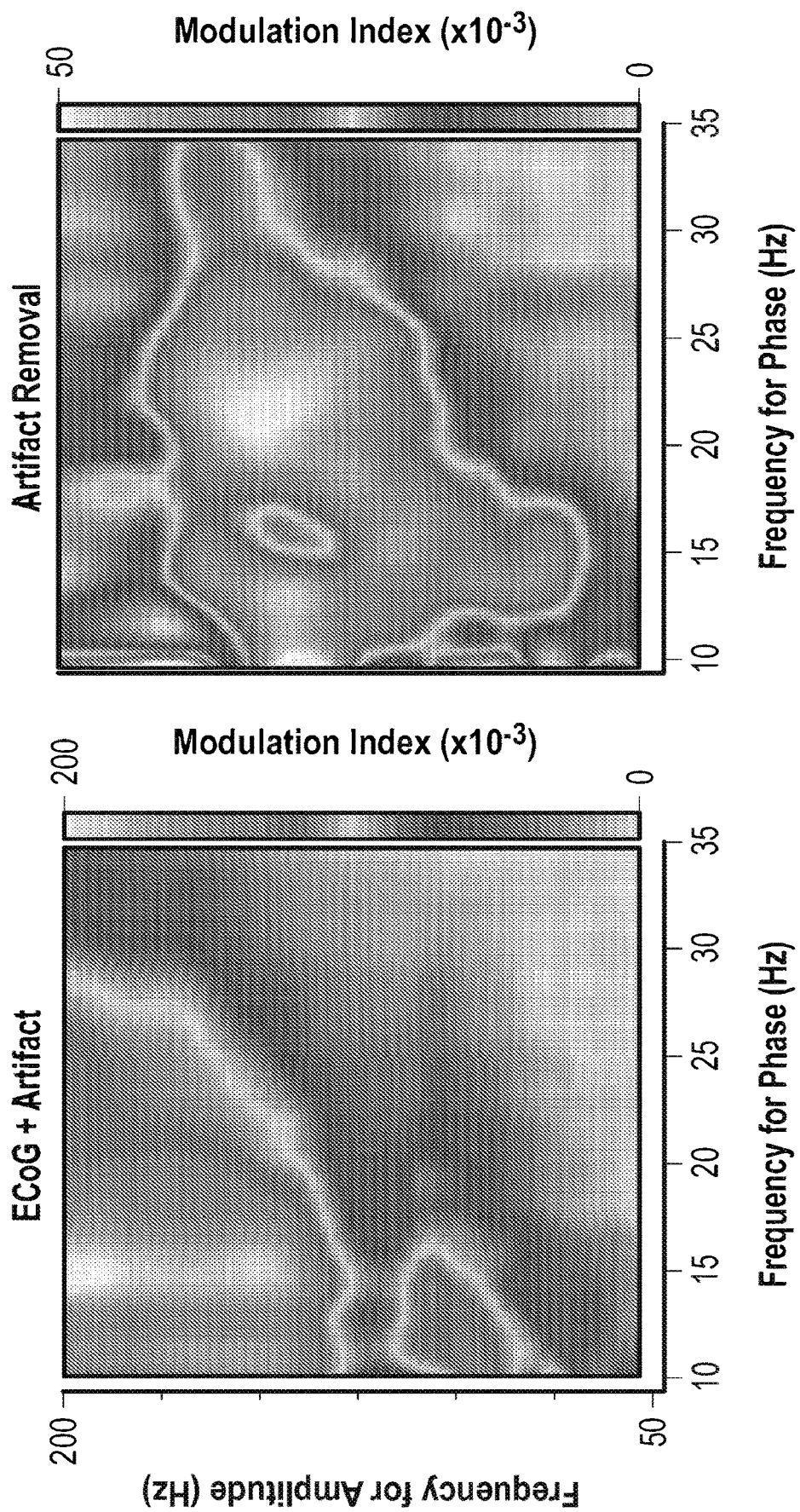

FIGS. 10A-10B are diagrams relating to example implementations described herein.

Stimulus induced artifacts may alter MI estimation and may significantly change calculated PAC levels. Stimulus artifact removal may reduce the induced PAC changes making it more representative of actual cortical network behavior. As shown in FIG. 10A, to reduce or eliminate the stimulus artifact from recordings, an optimized auto-regressive (AR) model (or another model) may be utilized for predicting the recorded signal during stimulation events. The predicted signal may be substituted for the stimulus artifact during active stimulation. Here, an example of stimulus artifact removal utilizing the predicted signals from the AR model is illustrated. The start time may be synchronized with the stimulation trigger and the stop time may be estimated based on the stimulus artifact duration. FIG. 10B shows an example of a sample of the MI estimation and an associated correction after removing the stimulus artifacts.

As indicated above, FIGS. 10A-10B are provided merely as one or more examples. Other examples may differ from what is described with regard to FIGS. 10A-10B.

Figure 11:
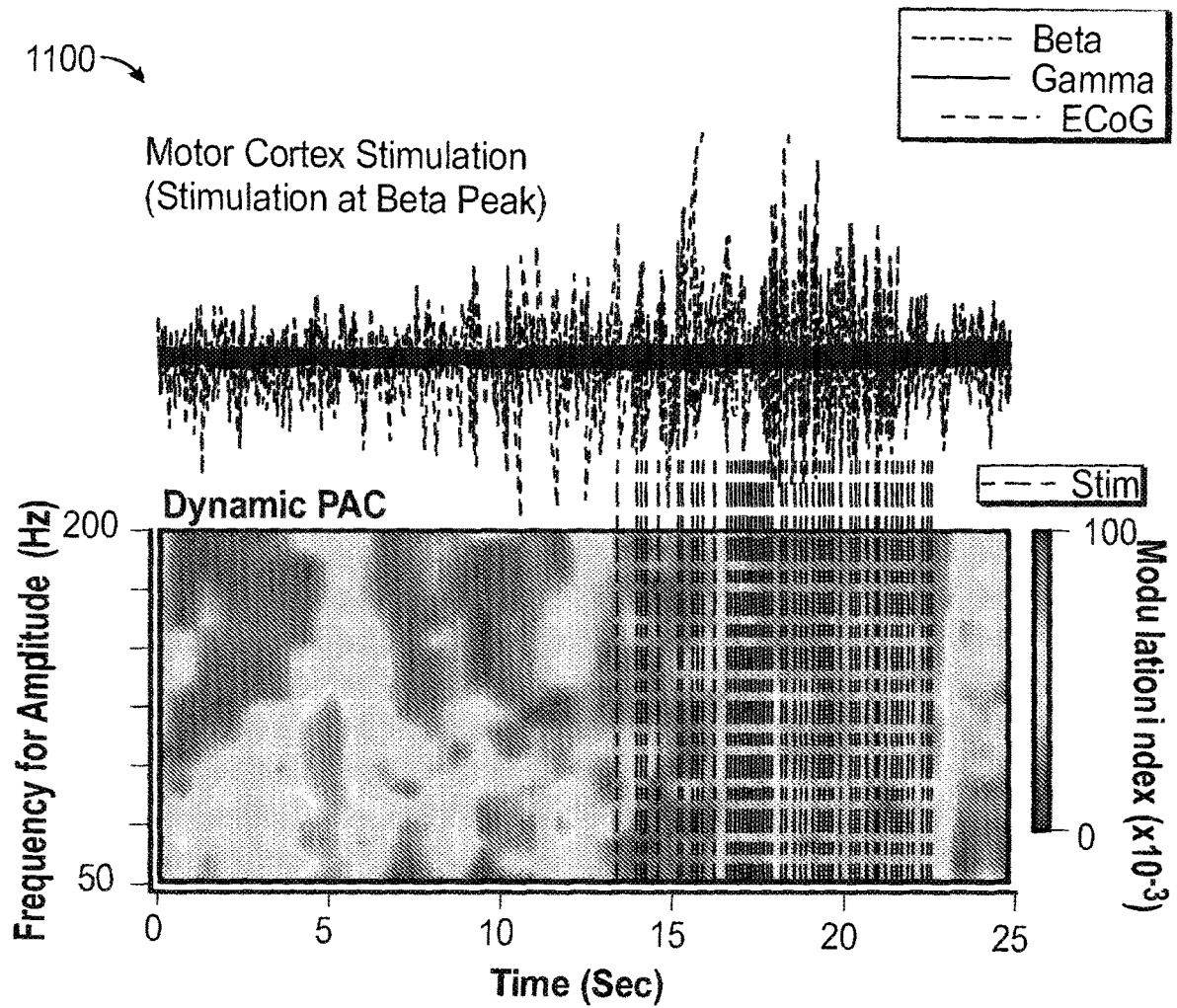

FIG. 11 is a diagram 1100 relating to example implementations described herein.

FIG. 11 shows an example of dynamic presentation of the phase-dependent stimulation. For example, diagram 110 includes an example period of real-time monitoring of PAC before, during, and after phase-dependent stimulation targeting peak of beta oscillations. In this case, the heat map represents the modulation index intensity as a measure of PAC between the phase of the beta oscillation and the amplitude of the gamma oscillation, with stimulation events (Stim) shown.

As indicated above, FIG. 11 is provided merely as an example. Other examples may differ from what is described with regard to FIG. 11.

Figure 12:
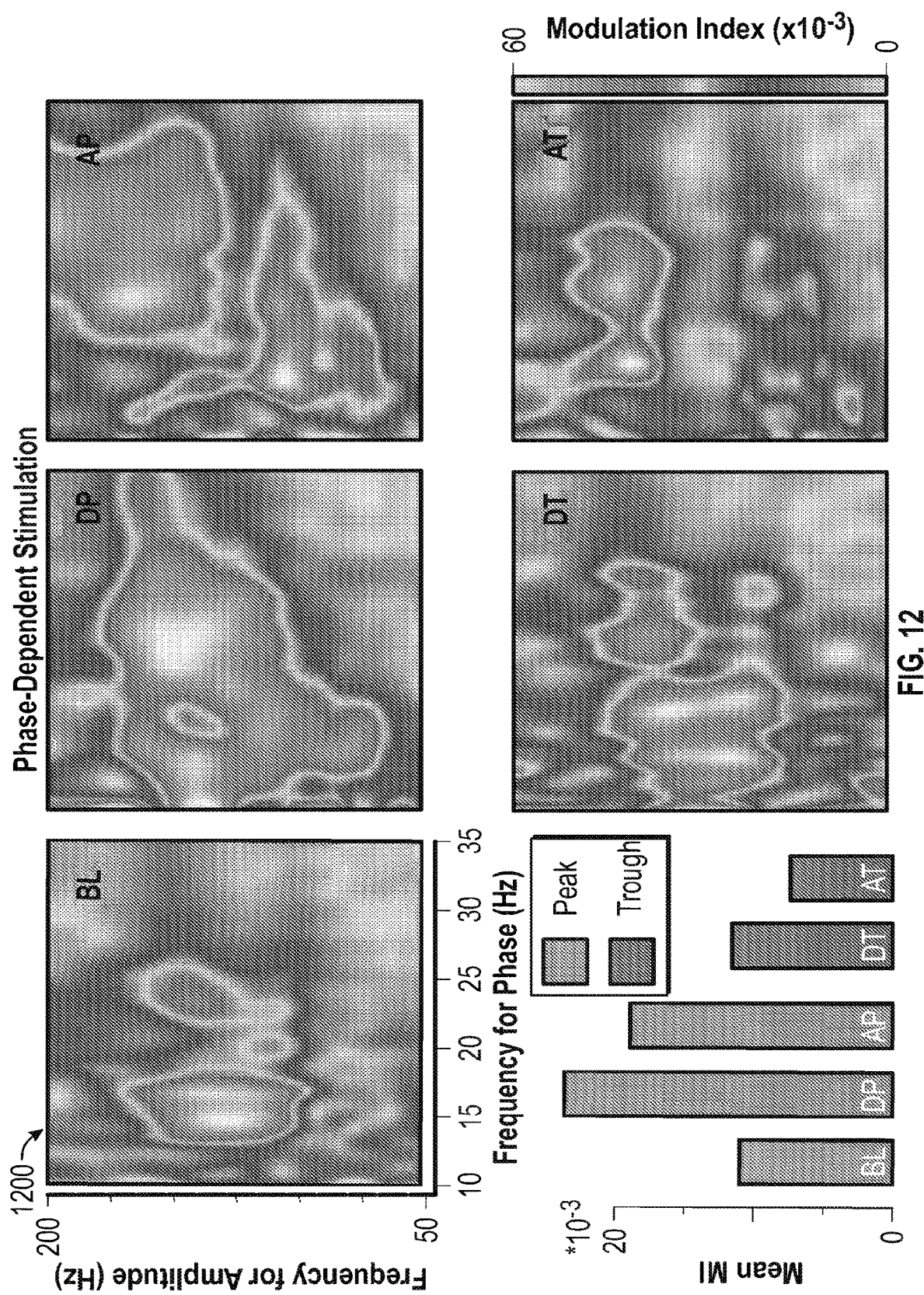

FIG. 12 is a diagram 1200 relating to example implementations described herein.

FIG. 12 shows an example of PAC modulation as a result of beta phase-dependent stimulation. In this case, the level of the coupling quantified by the modulation index between the beta frequency phase and gamma frequency amplitude for sample subject are shown at baseline (BL), during peak (DP), after peak (AP), during trough (DT), and after trough (AT) beta phase-dependent stimulation over the primary motor cortex region that showed maximum PAC during baseline recording.

As indicated above, FIG. 12 is provided merely as an example. Other examples may differ from what is described with regard to FIG. 12.

Figure 13A:
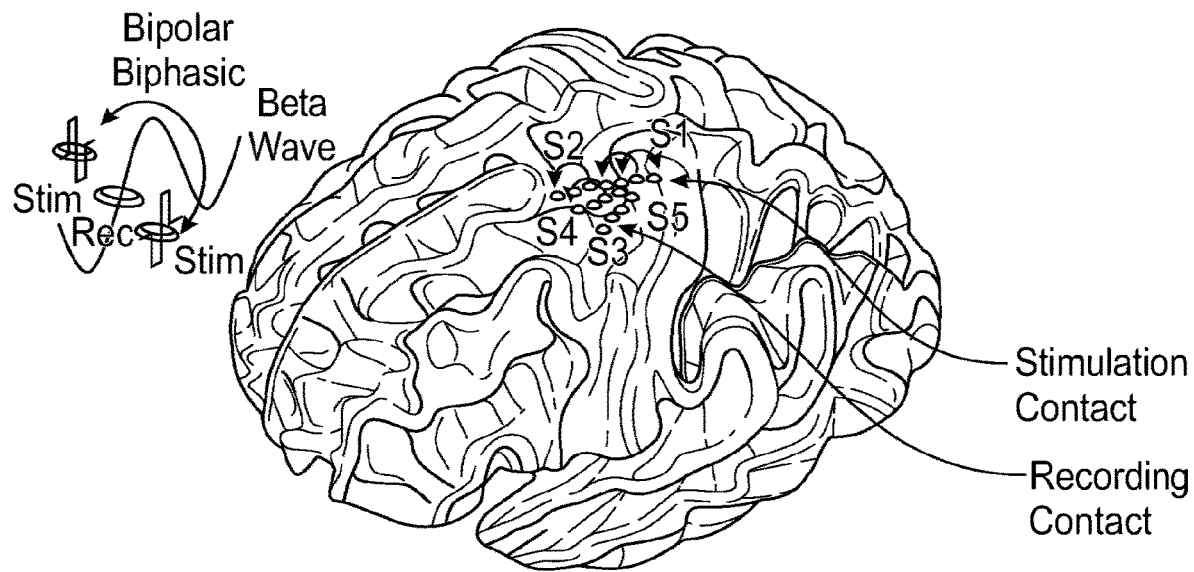
Figure 13B:
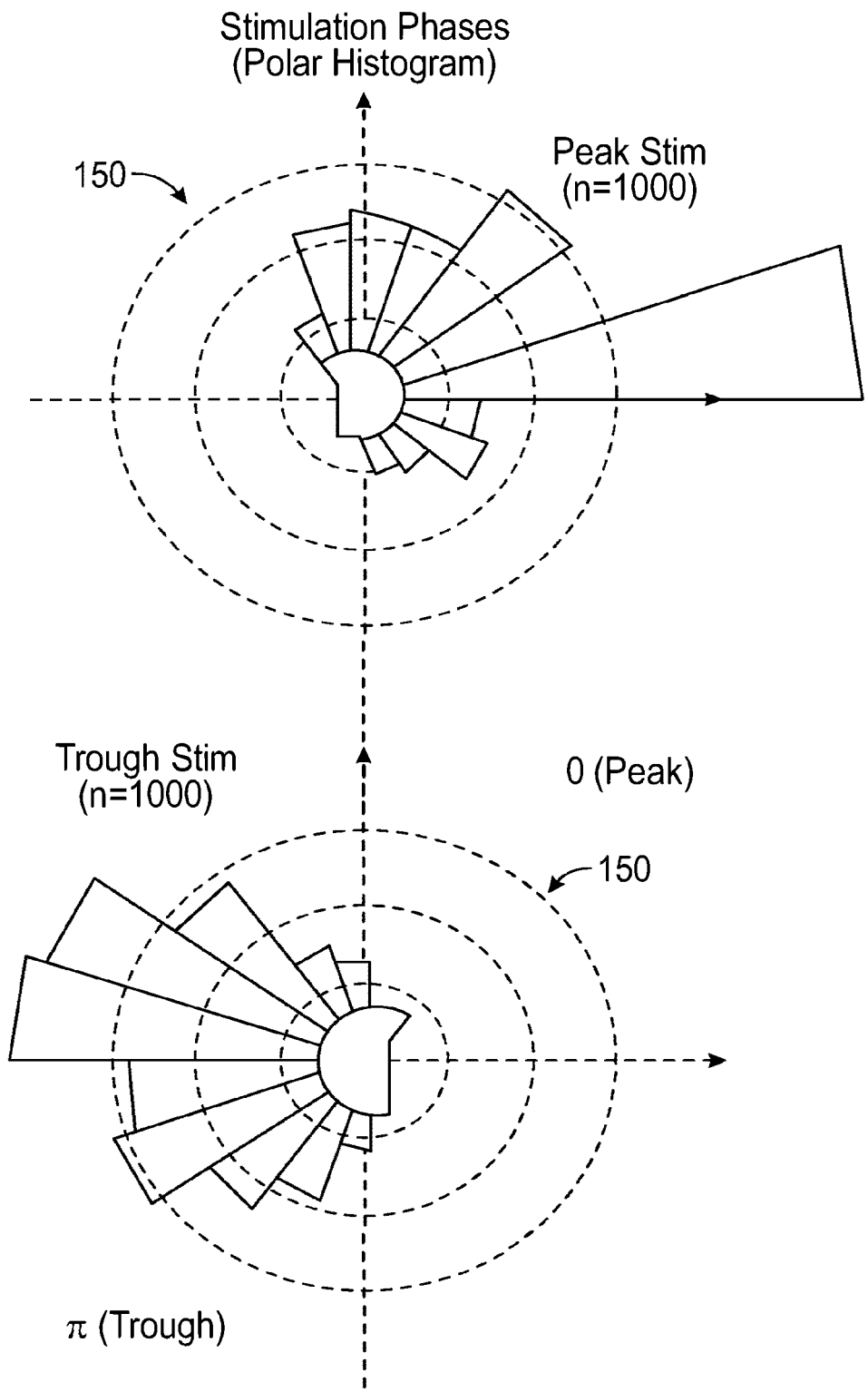
Figure 13C:
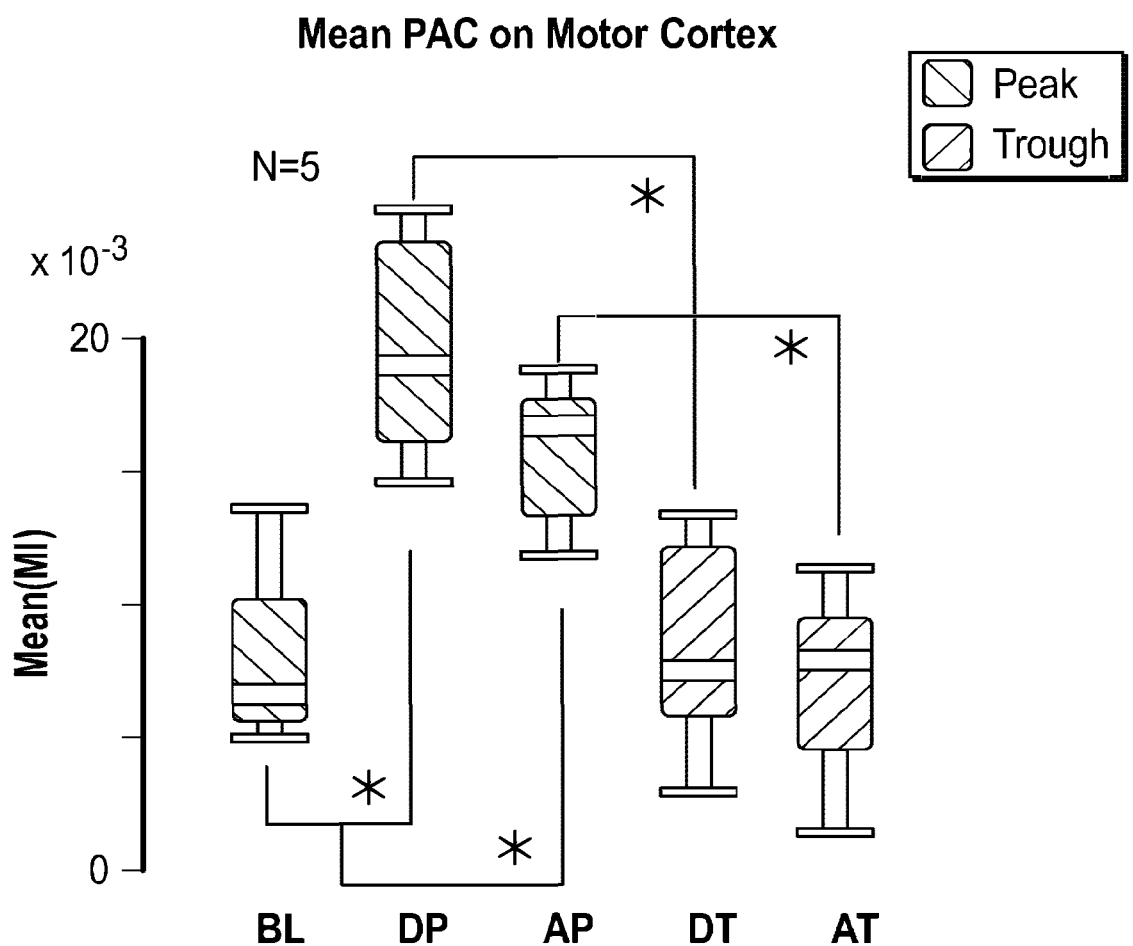

FIGS. 13A-13C are diagrams relating to example implementations described herein.

FIGS. 13A-13C show an example of PAC modulation in motor cortex. As shown in FIG. 13A electrode coordinates of the implanted cortical strip are estimated using imaging data. The relative location of the selected electrode contacts with respect to the site of recording are shown for all subjects. A recording contact, of a set of recording contacts, that is used for beta phase extraction is indicated as is a bipolar, biphasic stimulation contact of a set of stimulation contacts. FIG. 13B shows an example of the overall performance of the phase-dependent stimulation algorithm at the peak and trough are. In this case, the first 200 stimulation phases of each subject (e.g., with a total of 1000 data point for all subjects) at both peak and trough stimulation are shown. As shown in FIG. 13C a general trend of PAC changes as a result of phase-dependent stimulation is summarized in different testing phases of the stimulation paradigm including baseline (BL), during peak (DP), after peak (AP), during trough (DT), and after trough (AT). Here, the stars show statistically significant change in average PAC level based on the Wilcoxon signed-rank test (p value<0.05).

As indicated above, FIGS. 13A-13C are provided merely as one or more examples. Other examples may differ from what is described with regard to FIGS. 13A-13C.

Figure 14A:
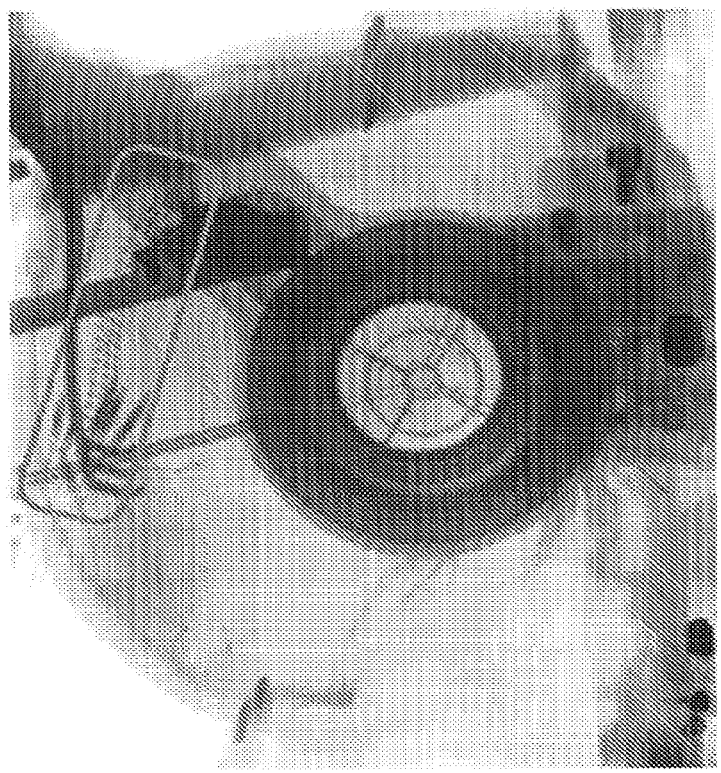
Figure 14B:
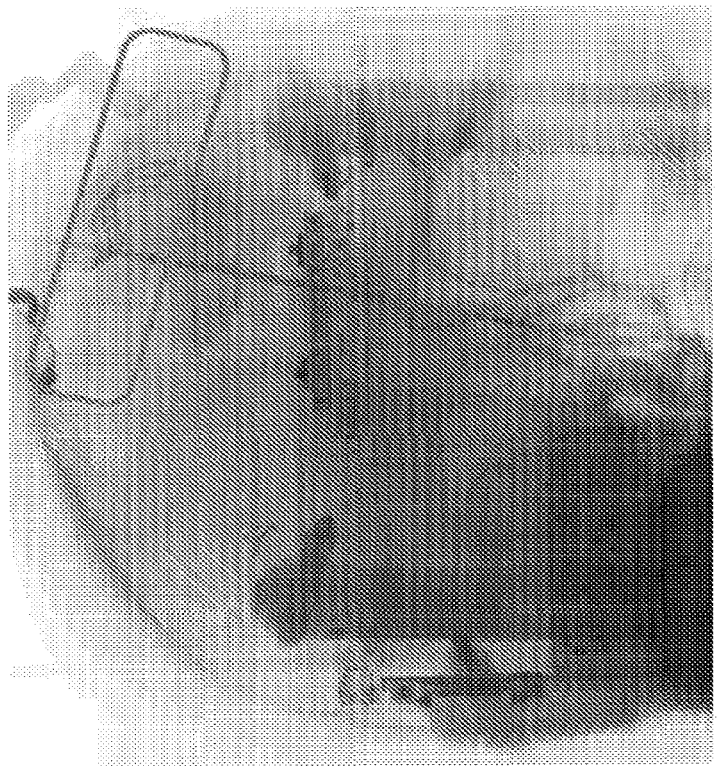
Figure 14C:
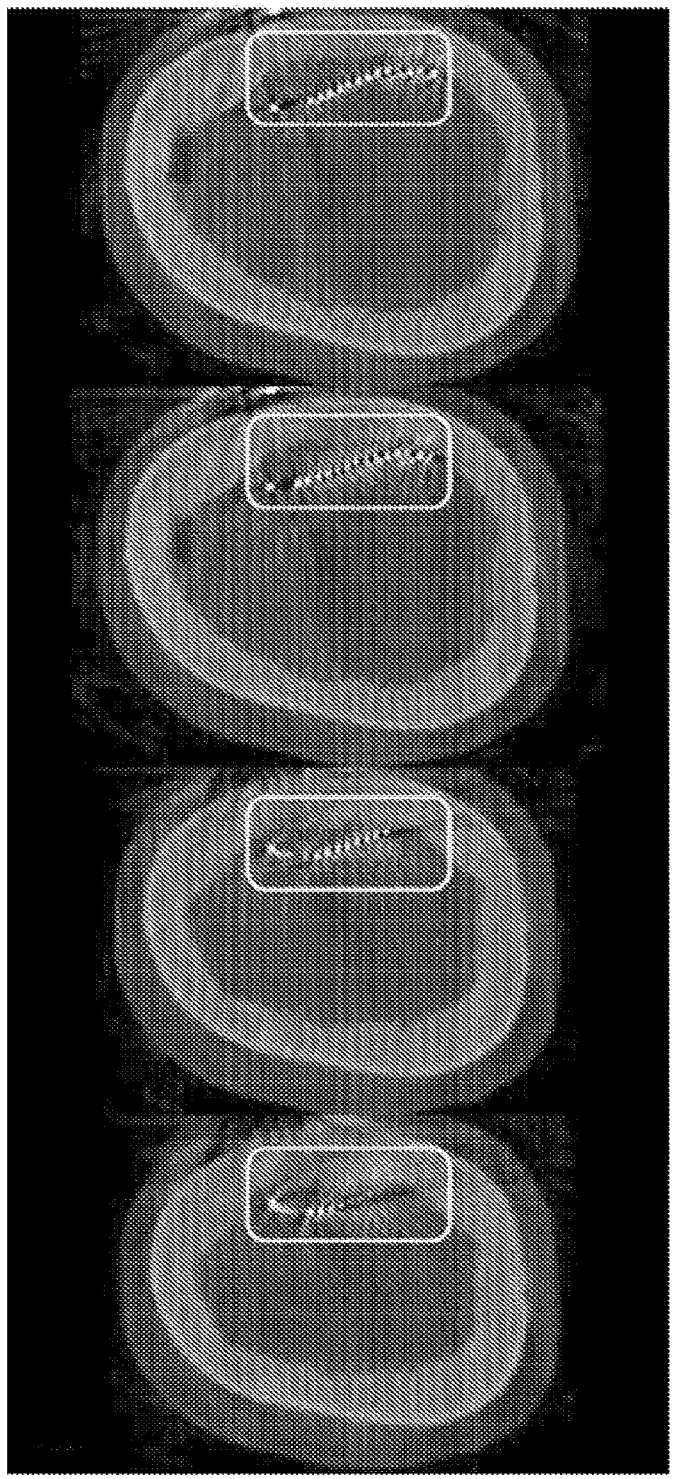

FIGS. 14A-14C are diagrams relating to example implementations described herein.

FIGS. 14A-14C show an electrode anatomical visualization. For example, FIGS. 14A-14C show an anatomical visualization of electrode placement accomplished using intraoperative fluoroscopy and computerized tomography (CT) scan imaging. Here, a set of neuroimaging visualizations for sample subject including intraoperative fluoroscopy (FIGS. 14A and 14B) and intraoperative CT scan (FIG. 14C) is shown.

As indicated above, FIGS. 14A-14C are provided merely as one or more examples. Other examples may differ from what is described with regard to FIGS. 14A-14C.

FIG. 15 is a diagram 1500 relating to example implementations described herein.

FIG. 15 shows demographic and clinical characteristics of patients. Patients are classified based on age (e.g., ranging from 56 to 74 in this case); sex (e.g., male (M) or female (F)); handedness and more symptomatic side (e.g., in terms of right (R) or left (L)); disease duration (in years); medications (e.g., milligrams (mg) of Levodopa equivalent dose (LED) per day); Hoehn and Yahr stage (e.g., which ranges from 1 to 5); Unified Parkinson Disease Rating Scale (UPDRS) score when off medication (e.g., which ranges from 0 to 199); UPDRS motor score when on medication; and a percentage improvement on medication relative to off medication for the UPDRS motor score.

As indicated above, FIG. 15 is provided merely as an example. Other examples may differ from what is described with regard to FIG. 15.

The foregoing disclosure provides illustration and description, but is not intended to be exhaustive or to limit the implementations to the precise forms disclosed. Modifications and variations may be made in light of the above disclosure or may be acquired from practice of the implementations.

As used herein, the term "component" is intended to be broadly construed as hardware, firmware, and/or a combination of hardware and software.

Some implementations are described herein in connection with thresholds. As used herein, satisfying a threshold may, depending on the context, refer to a value being greater than the threshold, more than the threshold, higher than the threshold, greater than or equal to the threshold, less than the threshold, fewer than the threshold, lower than the threshold, less than or equal to the threshold, equal to the threshold, or the like. For example, in some implementations, a threshold used by some implementations described herein may be an amplitude of a low frequency oscillation or a measure of a cross-frequency coupling, such as a phase-amplitude coupling between a phase of a low frequency rhythm and an amplitude of a high frequency oscillation.

User interfaces have been described herein and/or shown in the figures. A user interface may include a graphical user interface, a non-graphical user interface, a text-based user interface, and/or the like. A user interface may provide information for display. In some implementations, a user may interact with the information, such as by providing input via an input component of a device that provides the user interface for display. In some implementations, a user interface may be configurable by a device and/or a user (e.g., a user may change the size of the user interface, information provided via the user interface, a position of information provided via the user interface, etc.). Additionally, or alternatively, a user interface may be pre-configured to a standard configuration, a specific configuration based on a type of device on which the user interface is displayed, and/or a set of configurations based on capabilities and/or specifications associated with a device on which the user interface is displayed.

It will be apparent that systems and/or methods described herein may be implemented in different forms of hardware, firmware, or a combination of hardware and software. The actual specialized control hardware or software code used to implement these systems and/or methods is not limiting of the implementations. Thus, the operation and behavior of the systems and/or methods are described herein without reference to specific software code—it being understood that software and hardware can be designed to implement the systems and/or methods based on the description herein.

Even though particular combinations of features are recited in the claims and/or disclosed in the specification, these combinations are not intended to limit the disclosure of various implementations. In fact, many of these features may be combined in ways not specifically recited in the claims and/or disclosed in the specification. Although each dependent claim listed below may directly depend on only one claim, the disclosure of various implementations includes each dependent claim in combination with every other claim in the claim set.

No element, act, or instruction used herein should be construed as critical or essential unless explicitly described as such. Also, as used herein, the articles "a" and "an" are intended to include one or more items, and may be used interchangeably with "one or more." Furthermore, as used herein, the term "set" is intended to include one or more items (e.g., related items, unrelated items, a combination of related and unrelated items, etc.), and may be used interchangeably with "one or more." Where only one item is intended, the phrase "only one" or similar language is used. Also, as used herein, the terms "has," "have," "having," or the like are intended to be open-ended terms. Further, the phrase "based on" is intended to mean "based, at least in part, on" unless explicitly stated otherwise.

What is claimed is:

1. A method, comprising:
receiving, from one or more electrodes, information identifying brain activity for a first time period;

predicting, based on the information identifying the brain activity for the first time period, predicted brain activity for a second time period that is to occur after the first time period;

determining, based on the predicted brain activity for the second time period, a brain stimulus for the second time period, wherein the brain stimulus is associated with a frequency and a phase determined based on the predicted brain activity for the second time period, wherein the phase is a selected phase of a detected brain rhythmic activity and an associated cross-frequency coupling, and wherein the brain stimulus includes one or more pulses timed in accordance with a particular phase direction of the phase and the associated cross-frequency coupling; and causing the brain stimulus to be applied in accordance with the frequency and the phase during the second time period.

2. The method of claim 1, further comprising:

determining an artifact during the first time period associated with a prior brain stimulus;

determining an artifact-removed brain activity for the first time period based on the artifact; and wherein predicting the brain activity for the second time period further comprises:

predicting the brain activity for the second time period based on the artifact-removed brain activity.

3. The method of claim 1, wherein the brain stimulus is caused to occur during a period of rhythmic brain activity in accordance with the frequency and is locked to a particular phase of a low frequency oscillation.

4. The method of claim 1, wherein the brain stimulus is a variable-pulse stimulus.

5. The method of claim 1, wherein predicting the brain activity for the second time period further comprises:

predicting the brain activity using a parametric spectral estimation technique for modeling band limited oscillations.

6. The method of claim 1, wherein predicting the brain activity for the second time period comprises:

predicting the brain activity using a band-pass optimized autoregressive technique.

7. The method of claim 1, wherein the method is carried out by a first device that is external to a patient or a second device implanted into the patient.

8. A device, comprising:

one or more memories; and one or more processors communicatively coupled to the one or more memories, configured to:

receive, from one or more electrodes, information identifying brain activity for a first time period;

predict, based on the information identifying the brain activity for the first time period, first predicted brain activity for a second time period that is to occur after the first time period;

determine, based on the first predicted brain activity for the second time period, a first brain stimulus for the second time period, wherein the first brain stimulus is associated with a frequency and a phase determined based on the first predicted brain activity for the second time period, and wherein the device is configured to modulate cross-frequency coupling by using phase-dependent stimulation;

cause the first brain stimulus to be applied in accordance with the frequency and the phase during the second time period;

determine an artifact during the second time period associated with the first brain stimulus;

determine an artifact-removed brain activity for the second time period based on the artifact;

predict, based on the artifact-removed brain activity, second predicted brain activity for a third time period that is to occur after the second time period;

determine, based on the second predicted brain activity, a second brain stimulus; and cause the second brain stimulus to be applied during the third time period.

9. The device of claim 8, wherein the device is an external device connected to one or more electrodes disposed onto a brain of a patient.

10. The device of claim 8, wherein the device is a system-on-chip device at least partially implanted into a patient.

11. The device of claim 8, wherein the one or more processors are further configured to:

determine that the brain activity for the first time period satisfies a threshold; and where predicting the brain activity for the second time period comprises:

predict the brain activity for the second time period based at least in part on the brain activity for the first time period satisfying the threshold.

12. The device of claim 11, wherein the threshold is a beta activity threshold.

13. The device of claim 11, wherein the threshold is a phase amplitude coupling threshold.

14. The device of claim 13, wherein the one or more processors, when determining the brain activity, are configured to:

estimate a phase amplitude coupling in the first time period using a rolling dynamic phase amplitude coupling (PAC) estimation technique.

15. The device of claim 14, wherein the phase amplitude coupling is estimated in a window of less than or equal to 1 second.

16. The device of claim 14, wherein the phase amplitude coupling is estimated in a window of less than or equal to 500 milliseconds.

17. A system comprising, comprising:

one or more measurement electrodes;

one or more stimulus electrodes;

a control device connected to the one or more measurement electrodes and the one or more stimulus electrodes to:

receive information identifying brain activity for a first time period;

predict, based on the information identifying the brain activity for the first time period, predicted brain activity for a second time period that is to occur after the first time period;

determine, based on the predicted brain activity for the second time period, a brain stimulus for the second time period, wherein the brain stimulus is associated with a frequency and a phase determined based on the predicted brain activity for the second time period, and wherein the control device is configured to modulate cross-frequency coupling by using phase-dependent stimulation; and cause the brain stimulus to be applied in accordance with the frequency and the phase during the second time period.

18. The system of claim 17, wherein the control device is further configured to:
   determine an artifact during the first time period associated with a prior brain stimulus;
   determine an artifact-removed brain activity for the first time period based on the artifact; and
   predict the brain activity for the second time period based on the artifact-removed brain activity.

19. The system of claim 17, wherein the control device is further configured to:
   determine that the brain activity for the first time period satisfies a threshold; and
   predict the brain activity for the second time period based at least in part on the brain activity for the first time period satisfying the threshold.

20. The system of claim 17, wherein the brain stimulus is a pulse stimulus.

* * * * *